United States Patent [19]

Rosenfeld et al.

[11] Patent Number: 4,743,708

[45] Date of Patent: May 10, 1988

[54] PROCESS FOR THE SEPARATION OF $C_{10}$ AROMATIC ISOMERS

[75] Inventors: Daniel D. Rosenfeld, Houston; Lawrence G. Daniel, Crosby, both of Tex.

[73] Assignee: Exxon Chemical Patents Inc., Linden, N.J.

[21] Appl. No.: 843,220

[22] Filed: Mar. 24, 1986

Related U.S. Application Data

[63] Continuation-in-part of Ser. No. 716,208, Mar. 26, 1985, abandoned.

[51] Int. Cl.$^4$ .................................................. C07C 7/13
[52] U.S. Cl. .................................. 585/828; 208/310 Z
[58] Field of Search ...................... 208/310 Z; 585/828, 585/827, 831, 826, 824

[56] References Cited

U.S. PATENT DOCUMENTS

| 4,265,788 | 5/1981 | Ebitani et al. | 208/310 Z |
| 4,313,015 | 1/1982 | Broughton | 585/828 |
| 4,368,347 | 1/1983 | Carra et al. | 585/828 |
| 4,376,226 | 3/1983 | Rosenfeld et al. | 585/826 |
| 4,381,419 | 4/1983 | Wylie | 585/828 |
| 4,482,776 | 11/1984 | Rosenfeld et al. | 585/828 |
| 4,482,777 | 11/1984 | Neuzil | 208/310 Z |
| 4,529,828 | 7/1985 | Antos et al. | 585/828 |
| 4,542,254 | 9/1985 | Santacesaria et al. | 258/310 Z |
| 4,554,398 | 11/1985 | Barthomeuf et al. | 208/310 Z |
| 4,580,000 | 4/1986 | Wu | 208/310 Z |
| 4,584,424 | 4/1986 | Barthomeuf | 208/310 Z |

Primary Examiner—Helen M. S. Sneed
Assistant Examiner—Anthony McFarlane
Attorney, Agent, or Firm—M. D. Bittman; D. E. Furman

[57] ABSTRACT

A process for separating a $C_{10}$ aromatic isomer, particularly paradiethylbenzene, from a feedstream containing a mixture of $C_{10}$ aromatic isomers by contacting the feedstream with a bed of the adsorbent zeolite beta. The adsorbed $C_{10}$ aromatic isomer is removed from the adsorbent by desorption.

45 Claims, No Drawings

4,743,708

PROCESS FOR THE SEPARATION OF $C_{10}$ AROMATIC ISOMERS

CROSS REFERENCE TO RELATED APPLICATION

This application is a continuation-in-part of co-pending application Ser. No. 716,208 filed Mar. 26, 1985 now abandoned. All of the teachings of this prior application are incorporated herein by reference.

BACKGROUND OF THE INVENTION

The field of art to which the claimed invention pertains is hydrocarbon separations. More specifically, the claimed invention relates to the separation of a $C_{10}$ aromatic isomer from a hydrocarbon feedstream containing a mixture of $C_{10}$ aromatic isomers by use of the adsorbent zeolite beta which selectively removes a $C_{10}$ aromatic isomer from the feedstream. The selectively adsorbed $C_{10}$ aromatic isomer is removed from the adsorbent through a desorption step. In one embodiment, durene is selectively removed from a mixture of $C_{10}$ aromatic isomers containing the tetramethylbenzene isomers. In another embodiment, paradiethylbenzene is removed from a mixture of $C_{10}$ aromatic isomers containing the diethylbenzene isomers. In general, paradiethylbenzene is preferentially adsorbed over the other $C_{10}$ aromatic isomers. In one embodiment, paradiethylbenzene is preferentially adsorbed over the other $C_{10}$ aromatic isomers with an order for decreased preference of adsorption on zeolite beta as follows: paradiethylbenzene > durene > metadiethylbenzene > orthodiethylbenzene and prehnitene > isodurene.

DESCRIPTION OF THE PRIOR ART

It is known in the separation art that certain adsorbents generally comprising crystalline aluminosilicates can be utilized to separate certain hydrocarbons from mixtures thereof. In the separation of aromatic hydrocarbon isomers with certain crystalline alumiosilicates containing selected cations at the zeolitic cationic sites, selectivity of the zeolite for a given aromatic isomer is enhanced. This manner of separation is particularly useful when the components to be separated have similar physical properties, such as freezing or boiling points, which renders the components difficult to separate by distillation or crystallization.

A number of processes describing the separation of paraxylene from a mixture of at least one other xylene isomer utilizing a crystalline aluminosilicate adsorbent, are shown in U.S. Pat. Nos. 3,558,730, 3,558,732, 3,626,020, and 3,663,638.

Other processes which describe the adsorption separation of ethylbenzene from a mixture of xylene isomers utilizing a crystalline aluminosilicate adsorbent are shown in U.S. Pat. Nos. 3,943,182, 3,997,619, 3,998,901, and 4,021,499.

U.S. Pat. No. 3,793,385 discloses the use of the crystalline aluminosilicate zeolite beta to separate $C_8$ aromatic isomers, specifically to separate paraxylene and ethylbenzene from a mixture containing at least one other $C_8$ aromatic isomer.

U.S. Pat. No. 4,554,398 discloses a process for separating $C_9$ aromatic isomers from a feedstream containing a mixture thereof by contacting the feedstream with a bed of the adsorbent zeolite beta.

While the use of various zeolites to separate aromatic isomers is known, and the use of zeolite beta to separate $C_9$ aromatic isomers is known, less is known about adsorbents which effectively separate the $C_{10}$ aromatic isomers.

The $C_{10}$ aromatic isomers are useful in the chemical arts as desorbents in separation processes and as precursors in preparing other chemicals. More specifically, durene is used in organic synthesis and in the manufacture of plasticizers, polymers and fibers, and isodurene is also used in organic synthesis. Paradiethylbenzene is useful as an intermediate or solvent. However, the availability of these $C_{10}$ aromatic isomers is restricted due to the difficulty of effectively separating a $C_{10}$ aromatic isomer from a mixture of the $C_{10}$ aromatic isomers.

SUMMARY OF THE INVENTION

It is accordingly a broad objective of this invention to provide a process of separating a $C_{10}$ aromatic isomer from a hydrocarbon feedstream containing a mixture of $C_{10}$ aromatic isomers.

In brief, the invention comprises an adsorptive separation process for the separation of the $C_{10}$ aromatic isomers from a hydrocarbon feedstream containing a mixture of $C_{10}$ aromatic isomers by contacting the hydrocarbon feedstream with a bed of the adsorbent zeolite beta. A raffinate stream is then withdrawn from the bed, this stream containing less of the selectively adsorbed $C_{10}$ aromatic isomer. The adsorbed $C_{10}$ aromatic isomer on the bed is then desorbed to effect displacement of the isomer, followed by withdrawing from the adsorbent bed an extract stream containing the adsorbed $C_{10}$ aromatic isomer. The preferred zeolite beta adsorbent is cation exchanged to increase the $C_{10}$ aromatic selectivity of the adsorbent. In one embodiment, the preferred $C_{10}$ aromatic isomer is durene. In another embodiment, the preferred isomer is paradiethylbenzene. In general, paradiethylbenzene is preferentially adsorbed over the other $C_{10}$ aromatic isomers. In one embodiment, paradiethylbenzene is preferentially adsorbed over the other $C_{10}$ aromatic isomers with an order for decreased preference of adsorption on zeolite beta as follows: paradiethylbenzene > durene > metadiethylbenzene > orthodiethylbenzene and prehnitene > isodurene.

DETAILED DESCRIPTION OF THE INVENTION

Hydrocarbon feedstreams which can be utilized in the process of this invention contain mixtures of $C_{10}$ aromatic isomers. Specifically, these include the difficult-to-separate tetramethylbenzenes and dimethylethylbenzenes, and the diethylbenzenes. The tetramethylbenzene isomers include 1,2,4,5-tetramethylbenzene (durene), 1,2,3,5-tetramethylbenzene tetramethylbenzene (isodurene), and 1,2,3,4-tetramethylbenzene (prehnitene). The diethylbenzene isomers include 1,4-diethylbenzene (paradiethylbenzene), 1,3-diethylbenzene (meta-diethylbenzene) and 1,2-diethylbenzene (ortho-diethylbenzene). The close boiling points of these $C_{10}$ aromatic isomers (196° C., 197° C. and 204° C. for the tetramethylbenzene isomers; 181, 183, and 184 for the diethylbenezene isomers) render the isomers difficult to separate by distillation. Mixtures containing substantial quantities of $C_{10}$ aromatic isomers and other aromatics generally are produced by reforming processes, processes which are well known to the refining and petrochemical arts.

The hydrocarbon feedstream is contacted with a bed of the adsorbent, entitled zeolite beta. Zeolite beta and its method of manufacture are described in U.S. Pat. No. 3,308,069 and U.S. Pat. No. Re. 28,341 by Wadlinger et al., this disclosure being fully incorporated herein by reference. Also included with this definition of zeolite beta is where the aluminum is fully or partially substituted with the elements of gallium or boron to provide a gallosilicate or borosilicate, or where the silicon is fully or partially substituted with the elements of germanium, titanium or phosphorus but retains the same structure and similar X-ray diffraction pattern as defined in the Wadlinger et al. patents. After synthesizing the zeolite beta, it is necessary to calcine the zeolite at a temperature and for a time effective to remove any tetraethylammonium ions remaining after its synthesis. While the zeolite beta composition is fully described in this Wadlinger et al. patent, it has been surprisingly found that zeolite beta can be used to separate $C_{10}$ aromatic isomers from a feedstream containing a mixture of $C_{10}$ aromatic isomers. Further, the $C_{10}$ selectivity can be substantially increased by cation exchanging the zeolite beta with a suitable cation.

The process of this invention may be used to separate all the $C_{10}$ aromatic isomers from one another by the use of various stages or adsorption zones. The preferred separation is of paradiethylbenzene since it is the most strongly adsorbed $C_{10}$ aromatic isomer. In one embodiment the $C_{10}$ aromatic isomers are tetramethylbenzenes which are selectively adsorbed in the order of durene and prehnitene > isodurene, with either durene or prehnitene being preferentially adsorbed depending upon the particular cation exchanged form of the zeolite beta and the conditions of adsorption. In another embodiment the $C_{10}$ aromatic isomers are diethylbenzenes which are selectively adsorbed in the order of paradiethylbenzene > metadiethylbenzene and orthodiethylbenzene, with either metadiethylbenzene or orthodiethylbenzene being preferentially adsorbed depending on the particular cation exchanged form of zeolite beta and the conditions of adsorption. In general, paradiethylbenzene is preferentially adsorbed over the other $C_{10}$ aromatic isomers. In one embodiment, paradiethylbenzene is preferentially adsorbed over the other $C_{10}$ aromatic isomers with an order for decreased preference of adsorption on zeolite beta as follows: paradiethylbenzene > durene > metadiethylbenzene > orthodiethylbenzene and prehnitene > isodurene.

In order to substantially increase the selectivity of the adsorbent for $C_{10}$ aromatic isomers, the adsorbent which is available in its tetraethylammonium (TEA)-sodium form is preferably cation exchanged. After the TEA is removed the hydrogen-sodium form of zeolite beta can be exchanged with suitable cations which include base metal or transition metal cations, such as copper, rubidium, nickel, manganese, zinc, cobalt, potassium, cerium, barium, and cesium or mixtures thereof or other cations, such as ammonium. The preferred cations for increased selectivity of durene are hydrogen, sodium, cobalt and manganese with the most preferred cation being sodium. The preferred cation for increased selectivity of paradiethylbenzene is sodium. The zeolite beta can be exchanged with sodium by use of a sodium salt by caustic treatment with sodium hydroxide.

The zeolite beta absorbent can be combined with a binder, such as natural or synthetic clays (e.g., Kaolin), and inorganic oxides and can be in any form acceptable to the separation process such as extrudates, spheres, granules or tablets.

Certain characteristics of adsorbents are highly desirable, if not absolutely necessary, to the successful operation of a selective adsorption process. Among such characteristics are: absorptive capacity for some weight of the $C_{10}$ aromatic isomer per weight of adsorbent; and the selective adsorption of a $C_{10}$ aromatic isomer with respect to a raffinate component and the desorbent material.

Capacity of the adsorbent for adsorbing a specific volume of $C_{10}$ aromatic isomer is, of course, a necessity; without such capacity the adsorbent is useless for adsorptive separation. Furthermore, the higher the adsorbent's capacity for the $C_{10}$ aromatic isomer, the better is the adsorbent. Increased capacity of a particular adsorbent makes it possible to reduce the amount of adsorbent needed to separate the $C_{10}$ aromatic isomer contained in a particular charge of feed mixture. A reduction in the amount of adsorbent required for a specific adsorptive separation reduces the cost of the separation process. It is important that the good initial capacity of the adsorbent be maintained during actual use in the separation process over some economically desirable life. Generally, the adsorbent of this invention has a capacity of at least 3% of hydrocarbon by weight of adsorbent and preferably greater than 5% of hydrocarbon by weight of adsorbent.

The second necessary adsorbent characteristic is the ability of the adsorbent to separate components of the feed; or, in other words, that the adsorbent possess adsorptive selectivity, ($\alpha$), for one component as compared to another component. Relative selectivity can be expressed not only for one feed component as compared to another but can also be expressed between any feed mixture component and the desorbent material. The separation factor, ($\alpha$), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (\alpha) = \frac{[\text{weight } C/\text{weight } D]_A}{[\text{weight } C/\text{weight } D]_U}$$

where C and D are two components of the feed represented by weight, and the subscripts A and U represent the adsorbed and unadsorbed phases, respectively. The equilibrium conditions were determined when the feed passing over a bed of adsorbent did not change composition after contacting the bed of adsorbent. In other words, there was no net transfer of material occuring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the selectivity ($\alpha$) becomes less than or greater than 1.0 there is preferential adsorption by the adsorbent for one component with respect to the other. When comparing the selectivity by the adsorbent of one component C over component C, an ($\alpha$) larger than 1.0 indicates preferential adsorption of component C within the adsorbent. An ($\alpha$) less than 1.0 would indicate that component D is preferentially adsorbed leaving an unadsorbed phase richer in component C and an adsorbed phase richer in component D.

For optimum performance desorbent materials should have a selectivity equal to about 1 or less than 1 with respect to all extract components so that all of the extract components can be extracted as a class and all raffinate components clearly rejected into the raffinate stream. When the adsorbent of this invention is cation exchanged it is preferably exchanged with a cation which will impart an ($\alpha$) separation factor of at least 2.0 of the $C_{10}$ aromatic isomer (component C) over at least one of the other components (component D) of the hydrocarbon feedstream.

In order to test the various cation exchanged zeolite beta adsorbent materials with a particular feed mixture to measure the characteristics of adsorptive capacity and selectivity, a static testing procedure was employed. The procedure consisted of contacting a known weight of adsorbent with a known weight of mixed hydrocarbon feedstream. After allowing this mixture to reach equilibrium, a sample was removed and analyzed by gas chromatography. The amount of isomers in the raffinate were measured and the amount of isomers adsorbed were obtained by difference from the standard feedstream.

In a separation process, after the hydrocarbon feedstream is contacted with the bed of absorbent, a raffinate stream is withdrawn from the absorbent bed, this stream containing less of the selectively adsorbed $C_{10}$ aromatic isomer of the feedstream. Then the adsorbed aromatic isomer on the bed is desorbed to effect displacement thereof.

The desorbing step which can be used in the various processing schemes employing this adsorbent will vary depending on the type of operation employed. The term "desorbent material" as used herein shall mean any fluid substance capable of removing a selectively adsorbed $C_{10}$ aromatic isomer from the adsorbent. In the swingbed system in which the selectively adsorbed $C_{10}$ aromatic isomer is removed from the adsorbent by a purge stream, desorbent materials comprising gaseous hydrocarbons such as methane, ethane, etc., or other types of gases such as nitrogen or hydrogen may be used at elevated temperatures or reduced pressures or both to effectively purge the adsorbed $C_{10}$ aromatic isomer from the adsorbent.

However, in an adsorptive separation process which employs the adsorbent and which is generally operated at substantially constant pressures and temperatures to insure a liquid phase, the desorbent material relied upon must be judiciously selected to satisfy several criteria. First, the desorbent material must displace the $C_{10}$ aromatic isomer from the adsorbent with reasonable mass flow rates without itself being so strongly adsorbed as to unduly prevent the $C_{10}$ aromatic isomer from displacing the desorbent material in a following adsorption cycle. Expressed in terms of the selectivity, it is preferred that the adsorbent be more selective for a $C_{10}$ aromatic isomer with respect to a raffinate (e.g., other isomers), than it is for the desorbent material with respect to a raffinate. Secondly, desorbent materials must be compatible with the particular adsorbent and the particular feedstream. More specifically they must not reduce or destroy the critical selectivity of the adsorbent for the $C_{10}$ aromatic isomer with respect to the raffinate.

Desorbent materials to be used in the process of this invention should additionally be substances which are easily separable from the feedstream that is passed into the process. After desorbing the $C_{10}$ aromatic isomer of the feed, both desorbent material and the $C_{10}$ aromatic isomers are removed in a mixture from the adsorbent. Without a method of separating the desorbent material, such as distillation, the purity of either the $C_{10}$ aromatic isomer or the raffinate component would not be very high. It is therefore contemplated that any desorbent material used in this process will have a substantially different average boiling point than that of the feedstream. The use of a desorbent material having a substantially different average boiling point than that of the feed allows separation of desorbent material from feed components in the extract and raffinate streams by simple fractionation, thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture.

In a liquid-phase operation of the process of our invention, desorbent materials comprising mono-aromatic hydrocarbons are effective. Mixtures of the aromatic hydrocarbon with paraffins are also effective as desorbent materials. Such paraffins must be compatible with the adsorbent and feedstream as described above and must be easily separated from the feedstream. The paraffins can include straight or branched chain paraffins (such as heptane) or cycloparaffins which meet this criteria. Typical concentrations of aromatics in such mixtures can be from a few volume percent up to 100 volume % of the total desorbent material mixture but such concentrations preferably will be within the range of from about 50 volume % to about 100 volume % of the mixture. The desorbent may be benzene, diethylbenzene, xylenes, other polyalkylbenzenes, or more generally polycyclic hydrocarbons, etc., and mixtures thereof. The suitable desorbents include toluene and ethyltoluenes, with metaxylene or orthoxylene preferred as they provide increased separation and resolution of separation of the $C_{10}$ aromatic isomers.

Following desorption, the extract stream containing the $C_{10}$ aromatic isomer is withdrawn from the adsorbent bed. Depending on the separation factor ($\alpha$) this withdrawn extract can contain relatively pure fractions of $C_{10}$ aromatic isomer. However, it will be appreciated that the selectively adsorbed component is generally not completely adsorbed by the adsorbent, nor is the raffinate component generally completely non-adsorbed by the adsorbent.

In general, this adsorptive separation process can be carried out in the vapor or liquid phase, while the liquid phase is preferable. Adsorptive conditions for the process of this invention may include temperatures within the range of from about ambient to about 300° F. and will include pressures in the range from about atmospheric to about 500 psig. In a preferred embodiment the process is carried out in the liquid phase at temperatures of 90°-200° C. to lower the viscosity of the feedstream allowing for an increased flow rate or a reduction in the diameter of the adsorption column. Desorption conditions for the process of this invention shall generally include the same range of temperatures and pressures as described for the adsorptive operation. The desorption of the selectively adsorbed $C_{10}$ aromatic isomer could also be effected at subatmospheric pressures or elevated temperatures or both, or by vacuum purging of the adsorbent to remove the adsorbed isomer, but this process is not primarily directed to these desorption methods.

EXAMPLE I

A crystalline aluminosilicate zeolite beta adsorbent in its hydrogen form was cation exchanged with the cations as listed in Table I (the NaOH in parentheses indicates Na exchange was carried out with NaOH instead of a sodium salt). A $C_{10}$ aromatic feedstream containing 1% of durene, 2% of isodurene, 2% of prehnitene, and 0.5% of triisopropyl benzene (an internal standard for the gas chromatograph) with the remainder heptane, all by weight, was added at ambient temperature to the various cation exchanged zeolite beta adsorbents, with the amount of feedstream being in excess of that which the zeolite can adsorb. After allowing this mixture to reach equilibrium, the mixture was allowed to settle and a sample was removed and analyzed by gas chromatography. The amount of $C_{10}$ isomers in the raffinate was measured and the amount of isomers adsorbed was obtained by difference from the standard feedstream. The capacity and the ($\alpha$) separation factor were calculated for the tetramethylbenzene isomers as listed in Table I.

TABLE I

| Cation Form of Zeolite Beta | ($\alpha$) Separation Factor | | | Adsorption Capacity, wt % |
|---|---|---|---|---|
| | Durene/ Isodurene | Durene/ Prehnitene | Prehnitene/ Isodurene | |
| H | 5.9 | 3.3 | 1.8 | 6 |
| Na (NaOH) | 15.5 | 5.3 | 2.9 | 8 |
| Na | 9.1 | 3.9 | 2.4 | 7 |
| Co | 4.5 | 4.4 | 1.0 | 3 |
| Mn | 10.1 | 2.0 | 4.9 | 3 |
| Cs | 1.3 | 0.6 | 2.1 | 5 |
| Ce | 1.4 | 0.7 | 2.1 | 4 |
| Rb | 1.1 | 0.7 | 1.5 | 7 |
| Ni | 2.2 | 0.9 | 2.5 | 6 |
| Zn | 3.5 | 1.0 | 3.4 | 4 |
| Cu | 2.2 | 0.6 | 3.9 | |
| Ba | 6.9 | 0.8 | 8.6 | 4 |

As can be seen from Table I, the sodium exchanged form of zeolite beta was highly effective in the separation of durene from the other tetramethylbenzene isomers.

EXAMPLE II

In two runs a sample of a $C_{10}$ aromatic feed (b.p. 192°–202° C.) was obtained from a plant which contained 44.1 wt% of the three isomeric tetramethylbenzenes, 18.4 wt% of the dimethylethylbenzenes, 1.4 wt% napthalene as well as 36.1 wt% of five other unidentifiable components (components 1–5). The feed was added to a sodium exchanged aluminosilicate zeolite beta adsorbent as in Example I. After allowing the mixture to reach equilibrium a sample was removed and analyzed by gas chromatography. The ($\alpha$) separation factors of durene to the other components of the feed are listed on the following Table II.

TABLE II

| | ($\alpha$) Separation Factor | |
|---|---|---|
| | Run 1 | Run 2 |
| Durene/Isodurene | 8.7 | 9.8 |
| Durene/Prehnitene | 3.8 | 3.6 |
| Durene/Component 1 | 4.4 | 4.4 |
| Durene/Component 2 | 19.1 | 22.8 |
| Durene/Component 3 | 24.2 | 22.4 |
| Durene/Component 4 | 4.2 | 4.1 |

TABLE II-continued

| | ($\alpha$) Separation Factor | |
|---|---|---|
| | Run 1 | Run 2 |
| Durene/Component 5 | 1.6 | 1.8 |
| Durene/(1,4-DM-2-EB) | 2.5 | 2.3 |
| Durene/(1,3-DM-4-EB) | 3.2 | 3.4 |
| Durene/(1,2-DM-3-EB) | 8.4 | 10.2 |
| Durene/(1,2-DM-4-EB) | 3.6 | 3.1 |
| Durene/(naphthalene) | 3.6 | — |

This experiment shows the sodium zeolite beta adsorbent is more selective to durene than to any of the other components of the plant feed.

Based on the separation factor of durene relative to the dimethylethylbenzene isomers it is apparent that sodium zeolite beta is selective to the dimethylethylbenzene isomers in in the following order of decreasing preference of adsorption on zeolite beta: durene > 1,4-dimethyl-2-ethylbenzene > 1,3-dimethyl-4-ethylbenzene and 1,2-dimethyl-1,4-ethylbenzene > 1,2-dimethyl-3-ethylbenzene.

EXAMPLE III

A crystalline gallosilicate zeolite beta adsorbent in its hydrogen form was cation exchanged with the cations as listed in Table III. A $C_{10}$ aromatic feedstream as in Example I was added and analyzed as in Example I. The ($\alpha$) separation factor was calculated for the tetramethylbenzene isomers as listed in Table III.

TABLE III

| Cation Form of Zeolite Beta | ($\alpha$) Separation Factor | | |
|---|---|---|---|
| | Durene/ Isodurene | Durene/ Prehnitene | Prehnitene/ Isodurene |
| H | 7.6 | 2.0 | 3.7 |
| Co | 3.5 | 1.4 | 2.5 |
| K | 1.4 | 0.9 | 1.6 |
| Na (NaOH) | 4.1 | 2.7 | 1.5 |

This experiment shows the gallosilicate zeolite beta adsorbent is effective in separating the tetramethylbenzene isomers.

EXAMALE IV

A sample of a $C_{10}$ aromatic feedstream containing equimolar amounts of durene, isodurene, prehnitene and metaxylene was added to a sodium exchanged aluminosilicate zeolite beta adsorbent at various temperatures in an amount equal to the capacity of the adsorbent. After agitation to reach equilibrium a gas phase sample was removed and analyzed by gas chromatography. From the peaks of the chromatograms the ($\alpha$) separation factors between the various components of the feedstream were measured. The capacity ranged from 18 to 22 wt%. The ($\alpha$) separation factor is listed on the following Table IV:

TABLE IV

| Temperature | ($\alpha$) Separation Factor | | |
|---|---|---|---|
| | Durene/ Isodurene | Durene/ Prehnitene | Durene/ Metaxylene |
| 60° C. | 11 | 6.8 | 7.5 |
| 80° C. | 9.2 | 6.5 | 5.3 |
| 140° C. | 6 | 5.1 | 2.5 |

EXAMPLE V

A three foot section of liquid chromatography tubing was packed with crystals of a sodium exchanged aluminosilicate zeolite beta adsorbent. A plant $C_{10}$ aromatic feed as in Example II was run through the column at 90° C. and was desorbed with a desorbent containing 100% metaxylene. The ($\alpha$) separation factor for durene/isodurene was 6.1 and for durene/prehnitene was 4.5. Durene was recovered at a purity of greater than 95% by weight of the $C_{10}$ aromatic feed.

EXAMPLE VI

A crystalline aluminosilicate zeolite beta adsorbent in its hydrogen form was cation exchanged with the cations listed in Table V. A $C_{10}$ aromatic feedstream containing 2.3% paradiethylbenzene, 2.3% metadiethylbenzene, 2.4% orthodiethylbenzene, 2.3% triisopropylbenzene and 90.7% n-heptane, all by weight, was added at ambient temperature (about 25° C.) to the various cation-exchanged zeolite adsorbents, with the amount of feedstream being in excess of that which the zeolite can adsorb. After allowing this mixture to reach equilibrium, the mixture was allowed to settle and a sample was removed and analyzed by gas chromatography. The amount of $C_{10}$ isomers in the raffinate was measured, and the amount of isomers was obtained by difference from the standard feedstream. The capacity and the ($\alpha$) separation factor were calculated for the diethylbenzene isomers as listed in Table V.

TABLE V

| Cation Form of Zeolite Beta | ($\alpha$) Separation Factor | | | Capacity, wt % | |
|---|---|---|---|---|---|
| | P-DEB/ O-DEB | P-DEB/ M-DEB | M-DEB/ O-DEB | DEB | TOT |
| Na | 2.6 | 3.0 | 0.9 | 10.5 | 10.5 |
| K | 1.5 | 4.0 | 0.4 | 12.5 | 12.5 |
| Cs | 1.0 | 3.5 | 0.3 | 10.1 | 10.1 |
| Ba | 0.9 | 2.7 | 0.3 | 8.1 | 8.1 |

The sodium exchanged form of zeolite beta is effective in the separation of paradiethylbenzene from the other diethylbenzene isomers.

EXAMPLE VII

The procedure of Example 1 was followed using a crystalline gallosilicate zeolite beta which was cation-exchanged with the cations listed in Table B. The ($\alpha$) separation factor was calculated for the diethylbenzene isomers as listed in Table VI.

TABLE VI

| Cation Form of Zeolite Beta | ($\alpha$) Separation Factor | | | Capacity, wt % | |
|---|---|---|---|---|---|
| | P-DEB/ O-DEB | P-DEB/ M-DEB | M-DEB/ O-DEB | DEB | TOT |
| K | 1.9 | 3.2 | 0.6 | 6.3 | 6.3 |
| Cs | 2.7 | 3.6 | 0.8 | 6.0 | 6.0 |

EXAMPLE VIII

A crystalline aluminosilicate zeolite beta adsorbent in its hydrogen form was cation exchanged with the cations listed in Table VII. A $C_{10}$ aromatic feedstream containing 2.3% paradiethylbenzene, 2.3% metadiethylbenzene, 2.4% orthodiethylbenzene, 2.3% triisopropylbenzene, 76.7% n-heptane and 14% of one of the desorbents indicated in Table VII, all by weight, was added at ambient temperature (about 25° C.) to the various cation-exchanged zeolite adsorbents, with the amount of feedstream being in excess of that which the zeolite can adsorb. After allowing this mixture to reach equilibrium, the mixture was allowed to settle and a sample was removed and analyzed by gas chromatography. The amount of $C_{10}$ isomers and desorbent in the raffinate was measured, and the amount of isomers and desorbent was obtained by difference from the standard feedstream. The capacity and the ($\alpha$) separation factor were calculated for the diethylbenzene isomers and desorbent as listed in Table VII.

TABLE VII

| Cation Form of Zeolite Beta | P/O | P/M | P/D | Capacity, wt. % | |
|---|---|---|---|---|---|
| | | | | DEB | TOT |
| Benzene | | | | | |
| Na | 2.5 | 1.4 | 2.0 | 5.2 | 12.1 |
| K | 1.6 | 2.6 | 0.5 | 2.8 | 14.8 |
| Cs | 0.8 | 1.4 | 0.2 | 1.4 | 11.1 |
| Ba | 1.5 | 3.7 | 0.7 | 1.7 | 7.8 |
| Toluene | | | | | |
| Na | 2.3 | 3.1 | 3.8 | 5.0 | 10.4 |
| K | 1.5 | 4.2 | 1.7 | 4.4 | 12.8 |
| Cs | 0.7 | 2.7 | 1.0 | 3.3 | 10.6 |
| Ba | 1.0 | 3.0 | 1.6 | 3.2 | 8.7 |
| Ethylbenzene | | | | | |
| Na | 2.5 | 3.8 | 1.9 | 4.7 | 13.8 |
| K | 2.6 | 22.9 | 1.2 | 3.3 | 14.1 |
| Cs | 1.5 | 10.8 | 0.7 | 2.3 | 11.6 |
| Ba | 1.2 | 51.0 | 1.1 | 2.4 | 8.8 |
| Paraxylene | | | | | |
| Na | 1.4 | 2.2 | 1.9 | 5.9 | 13.8 |
| K | 0.9 | 2.1 | 1.4 | 6.2 | 15.0 |
| Cs | 0.5 | 2.4 | 1.6 | 5.2 | 11.1 |
| Ba | 0.5 | 2.1 | 1.5 | 3.9 | 8.0 |
| Metaxylene | | | | | |
| Na | 2.5 | 3.3 | 9.0 | 7.8 | 11.3 |
| K | 1.5 | 4.7 | 8.9 | 9.4 | 13.4 |
| Cs | 1.2 | 5.3 | 9.5 | 7.2 | 10.0 |
| Ba | 1.0 | 3.4 | 5.1 | 6.0 | 9.3 |
| Orthoxylene | | | | | |
| Na | 3.1 | 3.0 | 4.8 | 6.4 | 11.4 |
| K | 2.7 | 6.9 | 6.4 | 7.2 | 12.1 |
| Cs | 2.3 | 7.4 | 5.2 | 5.5 | 9.8 |
| Ba | 1.7 | 4.8 | 4.1 | 4.5 | 8.0 |
| Paraethyltoluene | | | | | |
| Na | 1.4 | 2.2 | 1.5 | 4.3 | 11.5 |
| K | 0.7 | 2.1 | 1.1 | 5.2 | 14.2 |
| Cs | 0.5 | 2.0 | 1.1 | 4.8 | 12.3 |
| Ba | 0.4 | 1.9 | 1.1 | 3.9 | 9.2 |

The sodium exchanged form of the zeolite beta with orthoxylene desorbent is effective in the separation of paradiethylbenzene from the other diethylbenzene isomers.

When sodium zeolite beta is used as an adsorbent, and benzene or orthoxylene is the desorbent, metadiethylbenzene is preferentially adsorbed over orthodiethylbenzene.

EXAMPLE IX

The procedure of Example VIII was followed using a crystalline gallosilicate zeolite beta which was cation-exchanged with the cations listed in Table VIII. The ($\alpha$) separation factor was calculated for the diethylbenzene isomers and desorbent as listed in Table VIII.

TABLE VIII

| Cation Form of Zeolite Beta | P/O | P/M | P/D | Capacity, wt. % DEB | TOT |
|---|---|---|---|---|---|
| Benzene | | | | | |
| K | 1.3 | 13.9 | 0.5 | 1.0 | 6.2 |
| Cs | | ...(1)... | | | |
| Toluene | | | | | |
| K | 2.5 | 6.9 | 1.9 | 1.6 | 4.8 |
| Cs | 1.4 | 4.1 | 1.0 | 1.3 | 5.1 |
| Ethylbenzene | | | | | |
| K | | ...(1)... | | | |
| Cs | | ...(1)... | | | |
| Paraxylene | | | | | |
| K | 1.1 | 2.4 | 1.8 | 2.8 | 6.3 |
| Cs | 1.1 | 2.5 | 1.6 | 2.5 | 5.9 |
| Metaxylene | | | | | |
| K | 2.4 | 4.3 | 11.3 | 4.5 | 6.0 |
| Cs | 3.0 | 4.8 | 10.8 | 4.3 | 5.8 |
| Orthoxylene | | | | | |
| K | | ...(1)... | | | |
| Cs | | ...(1)... | | | |
| Paraethyltoluene | | | | | |
| K | 1.1 | 2.0 | 1.0 | 1.9 | 6.0 |
| Cs | 1.3 | 2.3 | 1.0 | 2.1 | 7.1 |

(1) No significant adsorption observed.

EXAMPLE X

A three foot section of liquid chromatography tubing was packed with particles of sodium zeolite beta. A feed comprising equal weights of triisopropylbenzene, paradiethylbenzene, metadiethylbenzene, orthodiethylbenzene, durene, isodurene and prehnitene, was run through the column at 90° C. and was desorbed with 100% orhtoxylene. 100% of the paradiethylbenzene present in the feedstream was recovered at a purity of 100%. 97% of the durene present in the feedstream was recovered as a separate product at a purity of 100%. The ($\alpha$) separation factors of the components were as follows:

TABLE IX

| | ($\alpha$) Separation Factor | |
|---|---|---|
| Component | P-diethylbenzene/ Component | Durene/ Component |
| Isodurene | 64 | 22 |
| Prehnitene | 21 | 7 |
| O—diethylbenzene | 21 | 7 |
| M—diethylbenzene | 13 | 4 |
| Durene | 3 | — |
| P—diethylbenzene | — | 0.3 |

What is claimed is:

1. An adsorptive separation process for separating paradiethylbenzene from a hydrocarbon feedstream containing a mixture of $C_{10}$ aromatic isomers comprising:
   (a) contacting said hydrocarbon feedstream with a bed of an adsorbent of zeolite beta;
   (b) withdrawing from said bed of adsorbent a raffinate stream containing less of the paradiethylbenzene;
   (c) desorbing the paradiethylbenzene to effect displacement thereof by passing through the bed a desorbent selected from the group consisting of paraffins, ethyltoluene, polycyclic hydrocarbons and mixtures thereof; and
   (d) withdrawing from the adsorbent bed an extract stream containing paradiethylbenzene.

2. Process of claim 1 wherein the mixture of $C_{10}$ aromatic isomers are diethylbenzene which are selectively adsorbed in the order of paradiethylbenzene > orthodiethylbenzene and metadiethylbenzene.

3. Process of claim 1 wherein the mixture of $C_{10}$ aromatic isomers comprises the diethylbenzene isomers.

4. Process of claim 3 wherein the adsorbent selectively adsorbs metadiethylbenzene over orthodiethylbenzene.

5. Process of claim 1 further characterized in that said adsorbent contains at least one cation selected from the group consisting of hydrogen, the Group I and Group II metals, and the transition metals.

6. Process of claim 5 wherein the adsorbent contains the cation sodium.

7. Process of claim 1 further characterized in that said adsorbent contains at least one cation which imparts an ($\alpha$) separation factor of at least 2.0 of paradiethylbenzene over at least one of the other components of the hydrocarbon feedstream.

8. Process of claim 1 wherein the zeolite beta adsorbent comprises a silicate chosen from the group consisting of aluminosilicate, borosilicate and gallosilicate.

9. Process of claim 8 wherein the silicon contained in said zeolite is fully or partially substituted with an element chosen from the group consisting of germanium, titanium and phosphorus.

10. Process of claim 1 wherein the zeolite beta adsorbent is an aluminosilicate.

11. Process of claim 1 wherein the separation is carried out in the liquid phase.

12. Process of claim 1 wherein the process is carried out in the vapor phase.

13. Process of claim 1 wherein the separation process is carried out at a temperature within the range of ambient to about 300° C. and a pressure within the range of atmospheric to 500 psig.

14. Process of claim 11 wherein the process is carried out at a temperature within a range of about 90° to about 200° C.

15. Process of claim 1 wherein the adsorbent is combined with a binder.

16. Process of claim 15 wherein the binder is selected from the group consisting of natural and synthetic clays and inorganic oxides.

17. Process of claim 1 further characterized in that said adsorbent has a capacity of at least 3% of hydrocarbon by weight of adsorbent.

18. Process of claim 1 wherein the mixture of $C_{10}$ aromatic isomers comprises the tetramethylbenzene isomers.

19. Process of claim 3 wherein the mixture of $C_{10}$ aromatic isomers additionally comprises the tetramethylbenzene isomers.

20. Process of claim 19 wherein durene is selectively adsorbed over metadiethylbenzene or orthodiethylbenzene.

21. Process of claim 18 wherein metadiethylbenzene is selectively adsorbed over prehnitene or isodurene.

22. An adsorptive separation process for separating durene from a hydrocarbon feedstream containing a mixture of $C_{10}$ aromatic isomers comprising tetramethylbenzene isomers, comprising:
   (a) contacting said hydrocarbon feedstream with a bed of adsorbent of zeolite beta;
   (b) withdrawing from said bed of adsorbent a raffinate stream containing less of the durene;

(c) desorbing the durene with a desorbent to effect displacement thereof; and (d) withdrawing from the adsorbent bed an extract stream containing durene.

23. Process of claim 22 wherein the mixture of $C_{10}$ aromatic isomers also contains dimethylethylbenzenes, which are selectively adsorbed in the order of 1,4-dimethyl-2-ethylbenzene > 1,2-dimethyl-4-ethylbenzene and 1,3-dimethyl-4-ethylbenzene > 1,2-dimethyl-3-ethylbenzene.

24. Process of claim 22 further characterized in that said adsorbent contains at least one cation selected from the group consisting of hydrogen, the Group I and Group II metals, and the transition metals.

25. Process of claim 22 wherein the adsorbent contains the cation sodium.

26. Process of claim 24 further characterized in that said adsorbent contains at least one cation which imparts an (α) separation factor of at least 2.0 of durene over at least one of the other components of the hydrocarbon feedstream.

27. Process of claim 22 wherein the desorbent is selected from the group consisting of toluene, benzene, dimethylbenzene, paraffin, ethyltoluene, diethylbenzene, polycyclic hydrocarbons and mixtures thereof.

28. Process of claim 22 wherein the zeolite beta adsorbent comprises a silicate chosen from the group consisting of aluminosilicate, borosilicate and gallosilicate.

29. Process of claim 28 wherein the silicon contained in said zeolite is fully or partially substituted with an element chosen from the group consisting of germanium and phosphorus.

30. Process of claim 22 wherein the zeolite beta adsorbent is an aluminosilicate.

31. Process of claim 22 wherein the separation is carried out at a temperature within the range of ambient to about 300° and a pressure within the range of atmospheric to 500 psig.

32. Process of claim 22 wherein the process is carried out in the liquid phase.

33. Process of claim 22 wherein the process is carried out in the vapor phase.

34. Process of claim 22 wherein the absorbent is combined with a binder.

35. Process of claim 32 wherein the process is carried out at a temperature within a range of about 90° to about 200° C.

36. Process of claim 34 wherein the binder is selected from the group consisting of natural and synthetic clays and inorganic oxides.

37. Process of claim 22 further characterized in that said adsorbent has a capacity of at least 3% of hydrocarbon by weight of adsorbent.

38. Process of claim 25 wherein the zeolite beta has been cation exchanged by use of a sodium hydroxide.

39. Process of claim 25 wherein the zeolite beta has been cation exchanged by use of a sodium salt.

40. Process of claim 22 wherein the adsorbent selectively adsorbs prehnitene over isodurene.

41. Process of claim 22 wherein the mixture of $C_{10}$ aromatic isomers additionally contains one or more diethylbenzene isomers selected from metadiethylbenzene and orthodiethylbenzene.

42. Process of claim 41 wherein the adsorbent selectively adsorbs metadiethylbenzene over prehnitene or isodurene.

43. An adsorptive process for separating paradiethylbenzene from a hydrocarbon feedstream containing a mixture of $C_{10}$ aromatic isomers comprising diethylbenzene and tetramethylbenzene isomers, the process comprising:

(a) contacting said hydrocarbon feedstream with a bed of an adsorbent of zeolite beta;

(b) withdrawing from said bed of adsorbent a raffinate stream containing less of the paradiethylbenzene;

(c) desorbing the paradiethylbenzene to effect displacement thereof by passing through the bed a desorbent selected from the group consisting of paraffins, ethyltoluene, polycyclic hydrocarbons and mixtures thereof; and (d) withdrawing from the adsorbed bed an extract stream containing the paradiethylbenzene.

44. Process of claim 43 wherein the adsorbent selectively adsorbs durene over metadiethylbenzene or orthodiethylbenzene.

45. Process of claim 43 wherein the adsorbent selectively adsorbs metadiethylbenzene over prehnitene or isodurene.

* * * * *